United States Patent
Silver

(12) United States Patent    (10) Patent No.: US 6,299,594 B1
(45) Date of Patent: Oct. 9, 2001

(54) VACUUM REGULATOR FOR A BREASTMILK PUMP

(75) Inventor: Brian H. Silver, Cary, IL (US)

(73) Assignee: Medela, Inc., McHenry, IL (US)

( * ) Notice: Subject to any disclaimer, the term of this patent is extended or adjusted under 35 U.S.C. 154(b) by 0 days.

(21) Appl. No.: 09/505,319

(22) Filed: Feb. 16, 2000

Related U.S. Application Data

(62) Division of application No. 08/931,316, filed on Sep. 16, 1997, now Pat. No. 6,110,140
(60) Provisional application No. 60/026,221, filed on Sep. 17, 1996.

(51) Int. Cl.[7] .................................................. A61M 1/06
(52) U.S. Cl. .............................................................. 604/74
(58) Field of Search .................................. 604/30, 32, 33, 604/35, 118, 119, 248, 249, 73–76, 184, 346, 313–316; D24/109, 113–115; 119/14.01, 14.05, 14.22, 14.23, 14.24, 14.44; 251/207, 208, 210, 343–345; 137/853; 285/7

(56) References Cited

U.S. PATENT DOCUMENTS

| | | |
|---|---|---|
| 1,228,451 | 6/1917 | Latts . |
| 1,509,226 | 9/1924 | Brown . |
| 1,805,675 | 5/1931 | Rudolph . |
| 2,419,795 | 4/1947 | Saunders ............................... 128/297 |
| 2,539,846 | 1/1951 | Lewis et al. ............................. 604/74 |
| 2,712,950 | 7/1955 | Siebert ....................................... 285/7 |
| 2,760,754 | 8/1956 | Gladstone . |
| 3,033,226 | 5/1962 | Allen ..................................... 251/345 |
| 3,472,488 | 10/1969 | Hastings ................................ 251/344 |
| 3,642,249 | 2/1972 | Cruise .................................... 261/342 |
| 3,782,385 | 1/1974 | Loyd ..................................... 128/281 |
| 3,977,405 | 8/1976 | Yanase .................................. 128/281 |
| 4,249,481 | 2/1981 | Adams ............................... 119/14.02 |
| 4,263,912 | 4/1981 | Adams ................................. 128/281 |
| 4,311,141 | 1/1982 | Diamond .............................. 128/281 |
| 4,323,067 | 4/1982 | Adams ................................. 128/281 |
| 4,466,461 | 8/1984 | Weiss .................................... 251/344 |
| 4,573,969 | 3/1986 | Schlensog et al. ..................... 604/74 |
| 4,583,970 | 4/1986 | Kirchner ................................. 604/74 |
| 4,673,388 | 6/1987 | Schlensog et al. ..................... 604/74 |
| 4,758,232 | 7/1988 | Chak .................................... 604/220 |
| 4,759,747 | 7/1988 | Alda et al. .............................. 604/74 |
| 4,772,262 | 9/1988 | Grant et al. ............................. 604/74 |
| 4,799,922 | 1/1989 | Beer et al. .............................. 604/74 |
| 4,813,932 | 3/1989 | Hobbs .................................... 604/74 |
| 4,857,051 | 8/1989 | Larsson ................................... 604/74 |
| 4,883,464 | 11/1989 | Morifuki ................................. 604/74 |
| 4,886,494 | 12/1989 | Morifuji ................................. 604/74 |

(List continued on next page.)

FOREIGN PATENT DOCUMENTS

| | | | |
|---|---|---|---|
| 251810 | 9/1948 | (CH) . | |
| G 87 14 995.9 | 11/1987 | (DE) | ............... A61M/1/06 |
| 0 162 358 | 11/1985 | (EP) | ............... A61M/1/06 |
| 0 733 376 A2 | 9/1996 | (EP) | ............... A61M/1/00 |
| 185521 | 9/1922 | (GB) . | |
| 271857 | 10/1927 | (GB) . | |
| 762701 | 12/1956 | (GB) . | |
| 2 127 293 A | 4/1984 | (GB) | ............... A61M/1/06 |
| 407293 | 12/1946 | (IT) . | |

OTHER PUBLICATIONS

Lawrence, Ruth A., M.D., Breastfeeding: A Guide for the Medical Profession.
Medela Hospital Catalog, 1992.
Specification, MEDAP Milchsauger P 6010.

*Primary Examiner*—Sharon Kennedy
(74) *Attorney, Agent, or Firm*—Baniak Pine & Gannon

(57) ABSTRACT

"An improved vacuum regulator for a breastmilk pump comprising a rotary member having an internal groove that is positionable over at least one port on a nub that is adapted to be in communication with a volume of a breast pump in which negative pressure is periodically generated."

8 Claims, 8 Drawing Sheets

U.S. PATENT DOCUMENTS

| | | | |
|---|---|---|---|
| 4,892,517 | 1/1990 | Yuan et al. | 604/74 |
| 4,929,229 | 5/1990 | Larsson | 604/74 |
| 4,964,851 | 10/1990 | Larsson | 604/74 |
| 5,007,899 | 4/1991 | Larsson | 604/74 |
| 5,009,638 | 4/1991 | Riedweg et al. | 604/74 |
| 5,071,403 | 12/1991 | Larsson | 604/74 |
| 5,295,957 | 3/1994 | Aida et al. | 604/74 |
| 5,749,850 | 5/1998 | Williams et al. | 604/74 |
| 5,784,750 | 7/1998 | Sankovic et al. | 285/7 |
| 6,004,288 * | 12/1999 | Hochstedler et al. | 604/74 |
| 6,042,560 * | 3/2000 | Niederberger | 604/74 |
| 6,093,168 * | 7/2000 | Mendenhall | 604/74 |

* cited by examiner

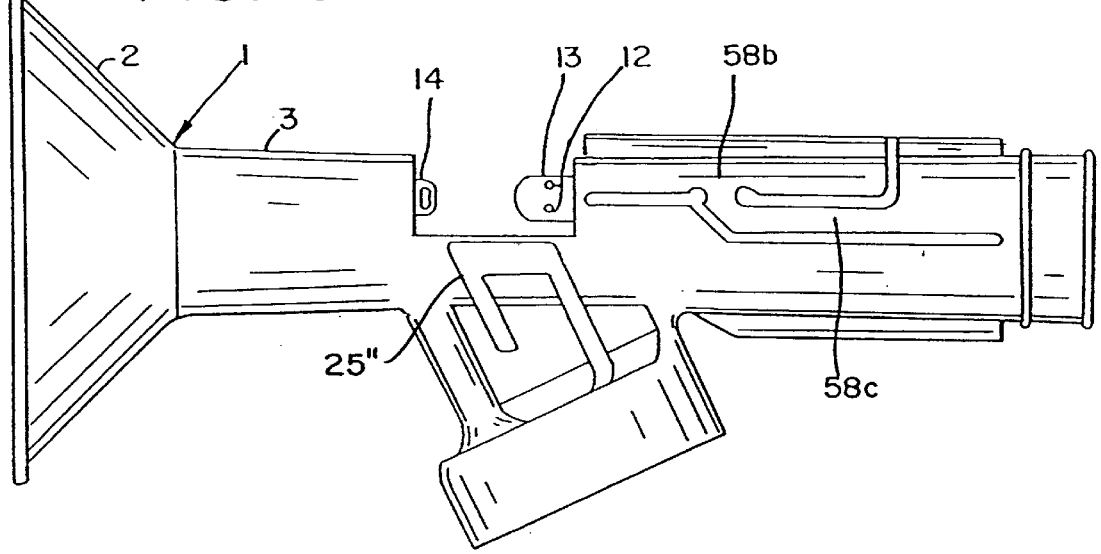
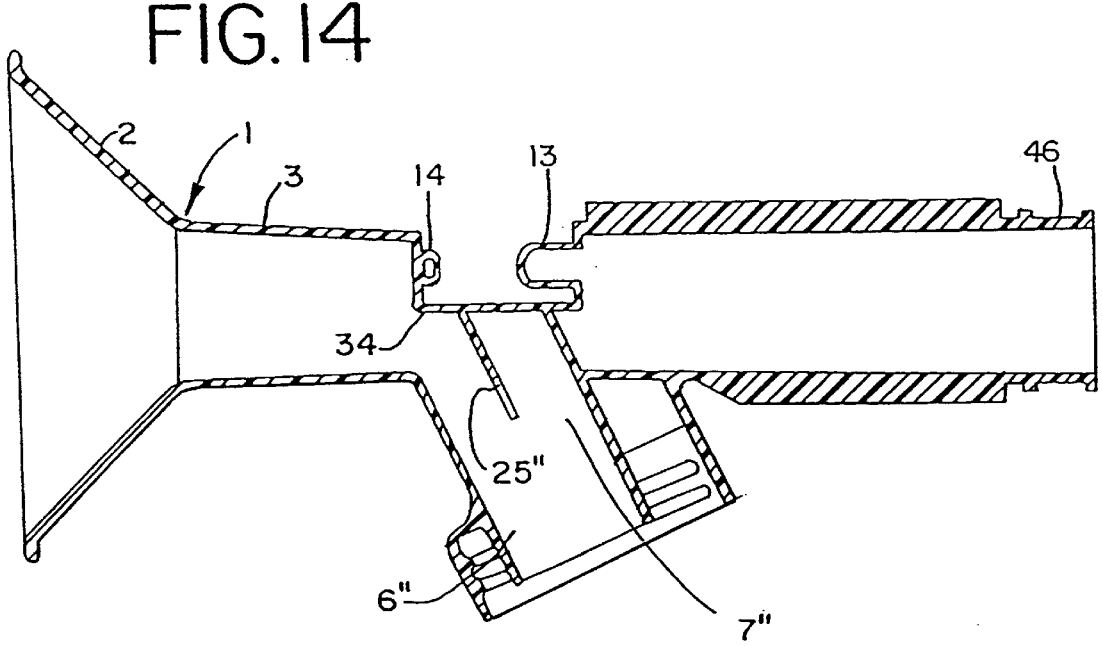
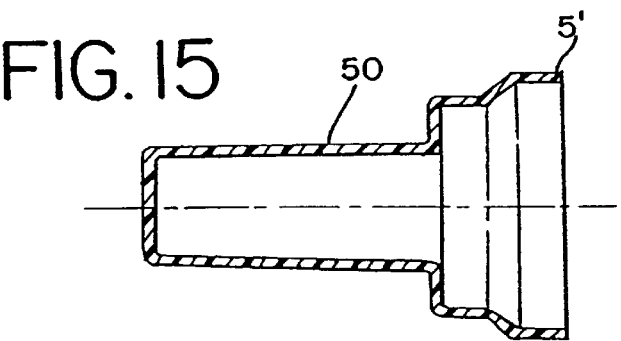

VACUUM REGULATOR FOR A BREASTMILK PUMP

This application is a division of U.S. application Ser. No. 08/931,316 filed on Sep. 16, 1997 and now U.S. Pat. No. 6,110,140, and claims priority to U.S. Provisional Application No. 60/026,221 filed Sep. 17, 1996.

FIELD OF THE INVENTION

The present invention generally relates to breastmilk pumps, and more particularly relates to a new and improved breastmilk pump with an effective and easy to operate manual pumping mechanism, a mechanism for one-handed or two-handed operation, and an improved vacuum regulator.

BACKGROUND OF THE INVENTION

Breastmilk pumps are well known and generally comprise a hood body or breast shield that fits over the breast, a vacuum pump connected to the hood body for generating an intermittent reduced pressure or vacuum within the hood body, and a receptacle for the expressed milk. Examples of these pumps are shown in U.S. Pat. No. 4,857,051 and U.S. Pat. No. 4,964,851.

An aspect of the design of a manually driven pump has been the amount of effort required to use the pump. As the user's hand tired, the suction created may decrease, as well as the stroke rate, thus decreasing the effectiveness of the pumping action. Manufacturing costs have also been a consideration because of numerous pieces that may be required in the construction of these pumps. Regulating the vacuum pressure created by the pumping action is also a consumer design consideration. Solutions to these problems are presented in this invention as are other innovations.

SUMMARY OF THE INVENTION

The present invention has a principal objective of providing a manual pump that is easy to operate. In one embodiment, vacuum is created by sliding a closed-end cylinder over a pump tube extending from the hood body. The user grasps the outer circumference of the cylinder and gently glides the cylinder over the pump tube. This pumping design is considered easier to manipulate than the traditional design of a movable piston rod reciprocating within a stationary cylinder. As applied to an inventive breast pump, the user generates reduced pressure or vacuum with a simple, nonstressful hand movement which utilizes better-suited muscle groups for pumping.

In addition, a locking means has been developed to prevent the cylinder from disengaging from the pump tube after reaching the position which generates the maximum reduced pressure (maximum stroke). The locking means is simple to engage or disengage, such as for cleaning of the pump elements.

Another objective of this invention is to provide an improved mechanism for regulating the vacuum created by the pumping action, which mechanism can be manipulated during use to adjust the amount of suction generated by a pumping stroke. One aspect of the present invention is having the regulator on the breast pump unit adjacent the hood body. A rotary member with an internal groove or passage communicating with the atmosphere connects to a ported structure and rotates about the structure to regulate the reduced pressure generated, by variously exposing the ports to ambient air. The reciprocating action of the cylinder over the pump tube then draws a predetermined amount of air through one or more of the ports to modify the amount of vacuum.

Also, while one of the goals of this invention is to provide a user with a handy, low-cost, low maintenance manual pump, aspects of this invention can be further modified to allow use with motor driven pumps.

In another embodiment of the invention, a lever drive mechanism is added to a piston-type pump configuration, which has a movable piston rod inside a stationary cylinder. The lever arrangement allows a user to operate the pump with one hand by grasping the lever and piston cylinder in one hand. As the lever is moved toward the cylinder, the piston rod slides toward the rear of the cylinder under action from the lever, creating a negative pressure in the pump. A spring action to return the lever, and the piston rod, to the starting position when the user releases the lever, can also advantageously be added. The relative position of the pump and lever makes the pump easy to operate and maintain its position on the breast.

In another aspect of the invention, a breast pump is adapted for use with one or both hands. Using the foregoing embodiment having the lever mechanism for one-handed operation as an example, the piston is provided with a hand-graspable part that extends out of the pump cylinder. The hand-graspable part can be reciprocated independently of the lever mechanism for two-handed operation. One-handed operation is provided by the lever mechanism, and another two-handed mode is provided by holding the pump in place with one hand and reciprocating the piston with the hand graspable part of the piston rod.

BRIEF DESCRIPTION OF THE DRAWINGS

FIG. 4 is an enlarged sectional view of the vacuum regulator taken along line 4—4 of FIG. 1;

FIG. 13 is an enlarged side elevational view of the pump tube and additional elements of FIG. 7;

FIG. 14 is a sectional view of the embodiment depicted in FIG. 13; and

FIG. 15 is an enlarged sectional view of the end piece depicted in FIG. 7.

DETAILED DESCRIPTION OF EMBODIMENTS OF THE INVENTION

Figure 1:
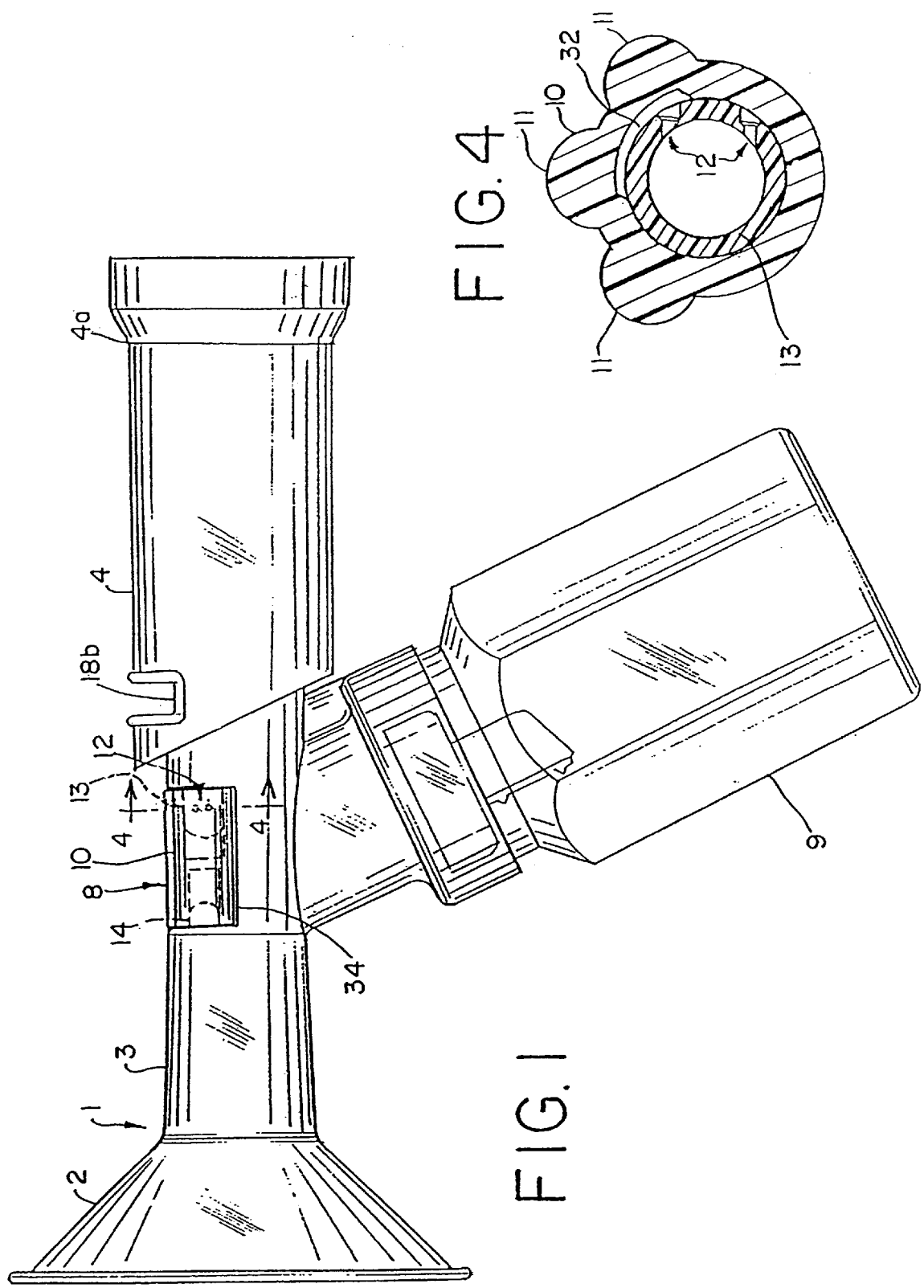
FIG. 1 is a side elevational view showing a first embodiment of an improved breast pump made in accordance with the present invention, with the cylinder engaged over the pump tube.
Figure 2:
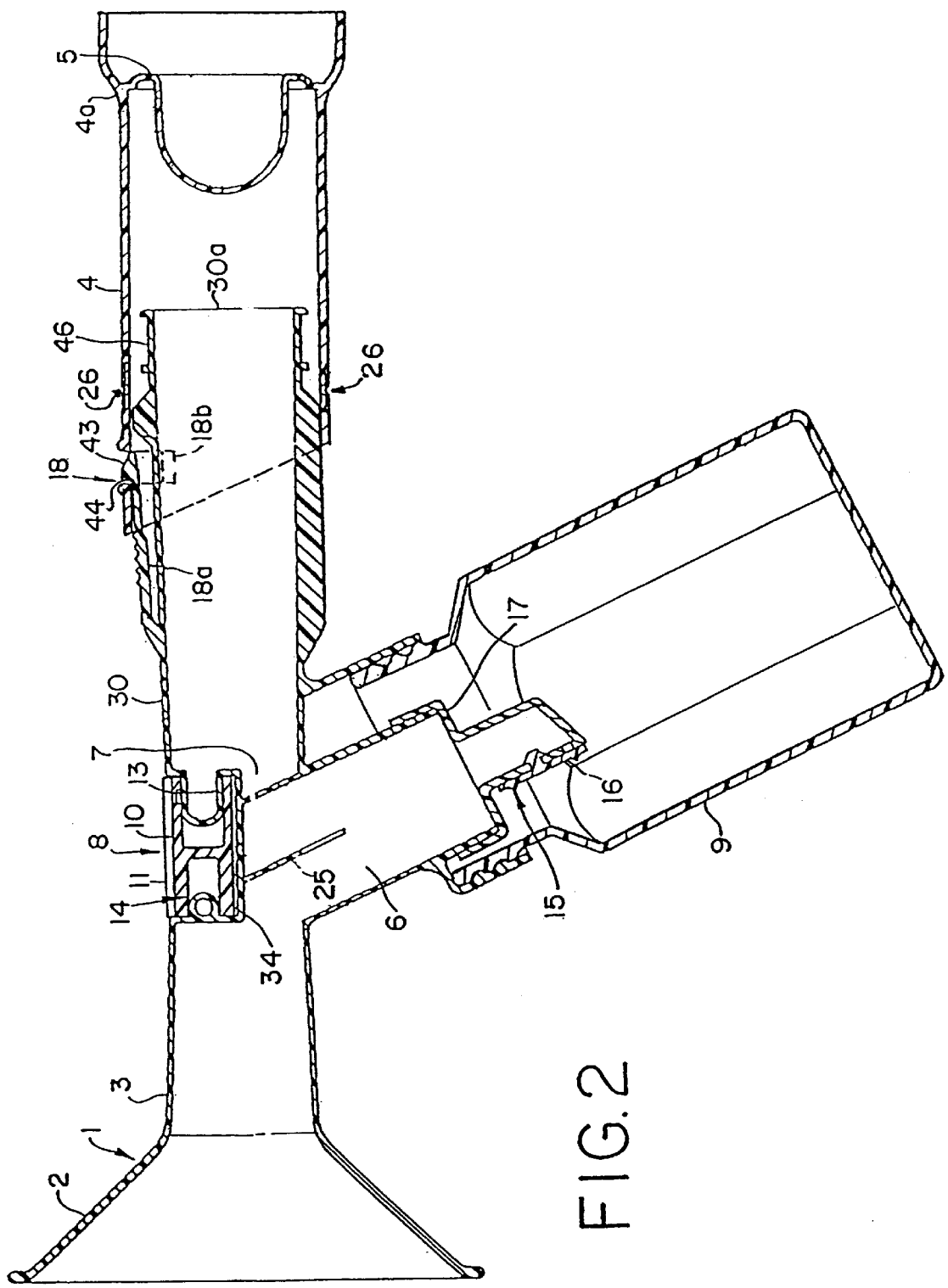
FIG. 2 is a sectional view of the embodiment of FIG. 1 with the cylinder reciprocated toward the rear end of the pump tube.
Figure 7:
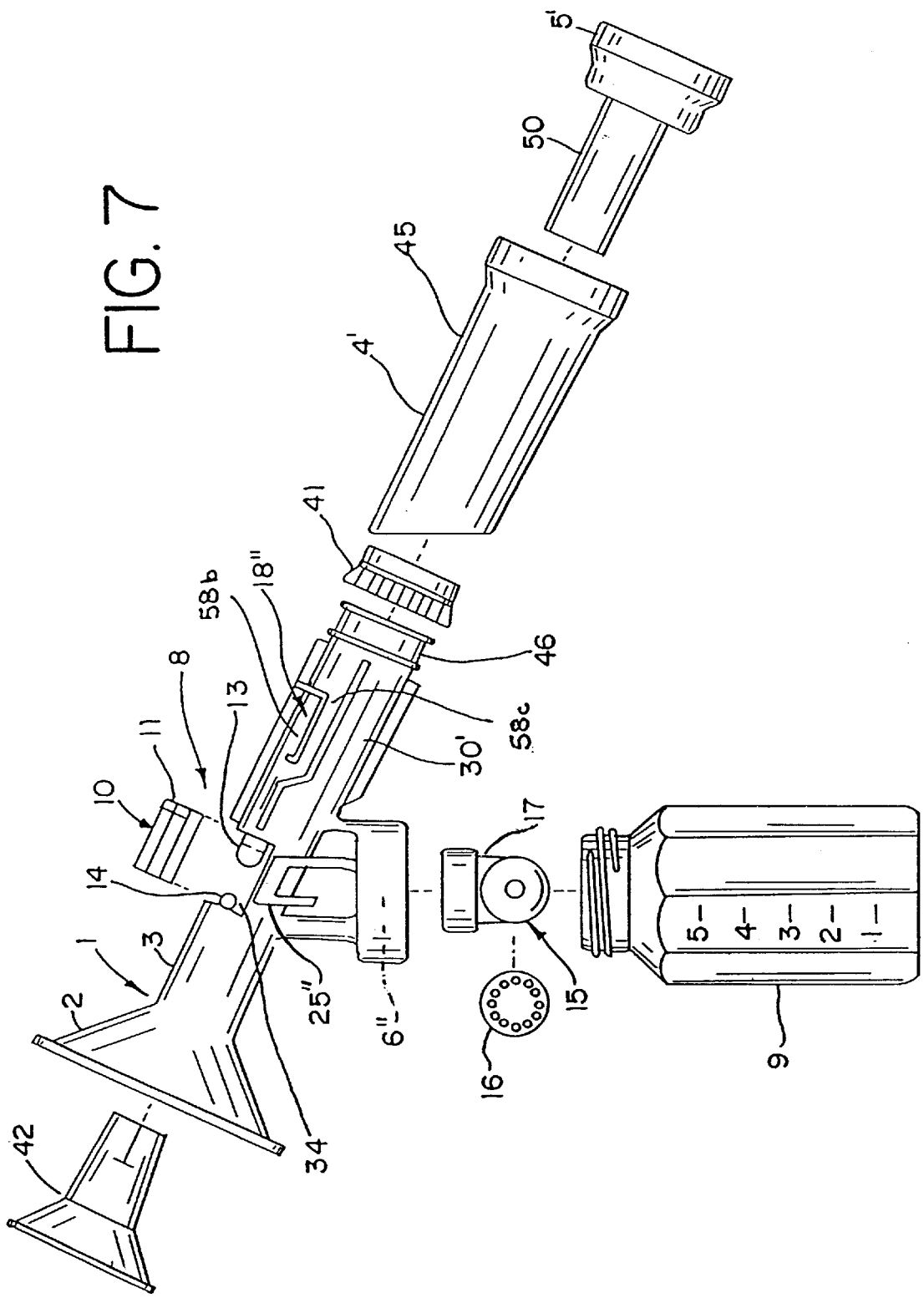
FIG. 7 is a side elevational view showing a third embodiment of an improved breast pump made in accordance with the present invention, showing the various parts comprising the breast pump.
Figure 8:
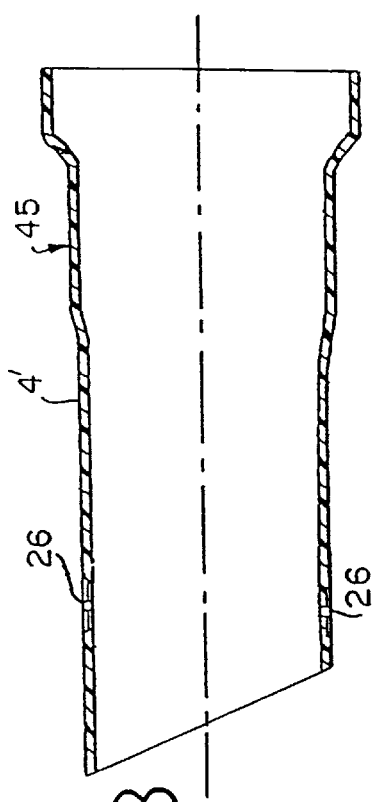
FIG. 8 is a sectional view of the cylinder of the third embodiment.
Figure 9:
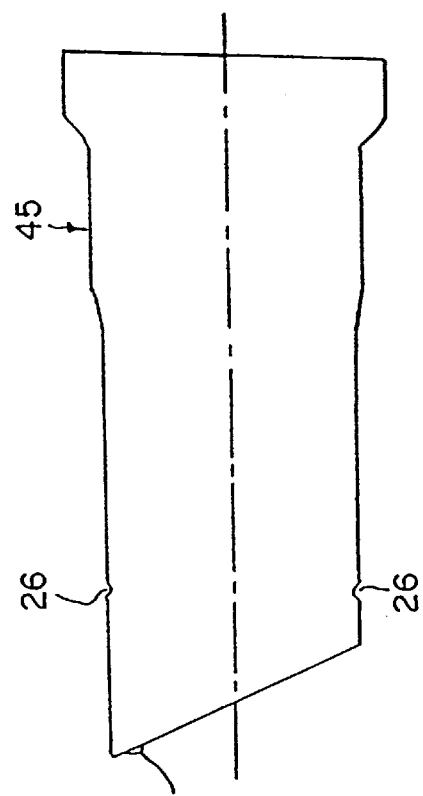
FIG. 9 is a side view of the cylinder of the third embodiment.
Figure 10:
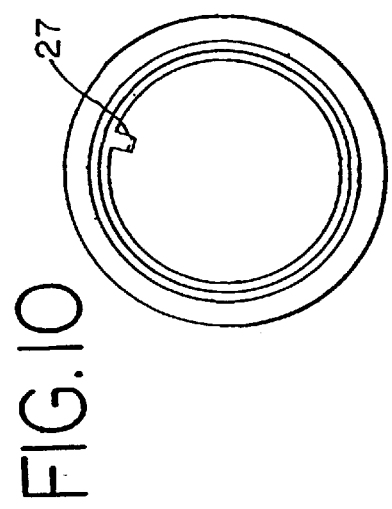
FIG. 10 is a frontal view of the cylinder of FIG. 9 showing the post extending downwardly therefrom.
Figure 11:
FIG. 11 is an enlarged sectional view of the post taken along line A—A of FIG. 10.
Figure 12:
FIG. 12 is a bottom view of the post of FIG. 11.

A first embodiment of a manually operable breast pump, as shown in FIGS. 1–4, has a hood body or shield 1 having two sections: a funnel shaped front section 2 and a tubular extension 3 extending therefrom. A vacuum regulator 8 is positioned on the hood body 1. A cylinder 4, in one embodiment, at its rearward portion 4a, has an end cap 5. The cylinder 4 is slidably engaged over a pump tube 30. When the cylinder 4 is reciprocated to the rear end 30a of the pump tube 30, as depicted in FIG. 2, reduced pressure or vacuum is created. A suitable substantially airtight engagement between the cylinder 4 and the pump tube 30 is provided as by a sliding interference-type fit, or a gasket or the like. The gasket (such as gasket 41 shown in FIG. 7) fits in annular groove 46.

Figure 3:
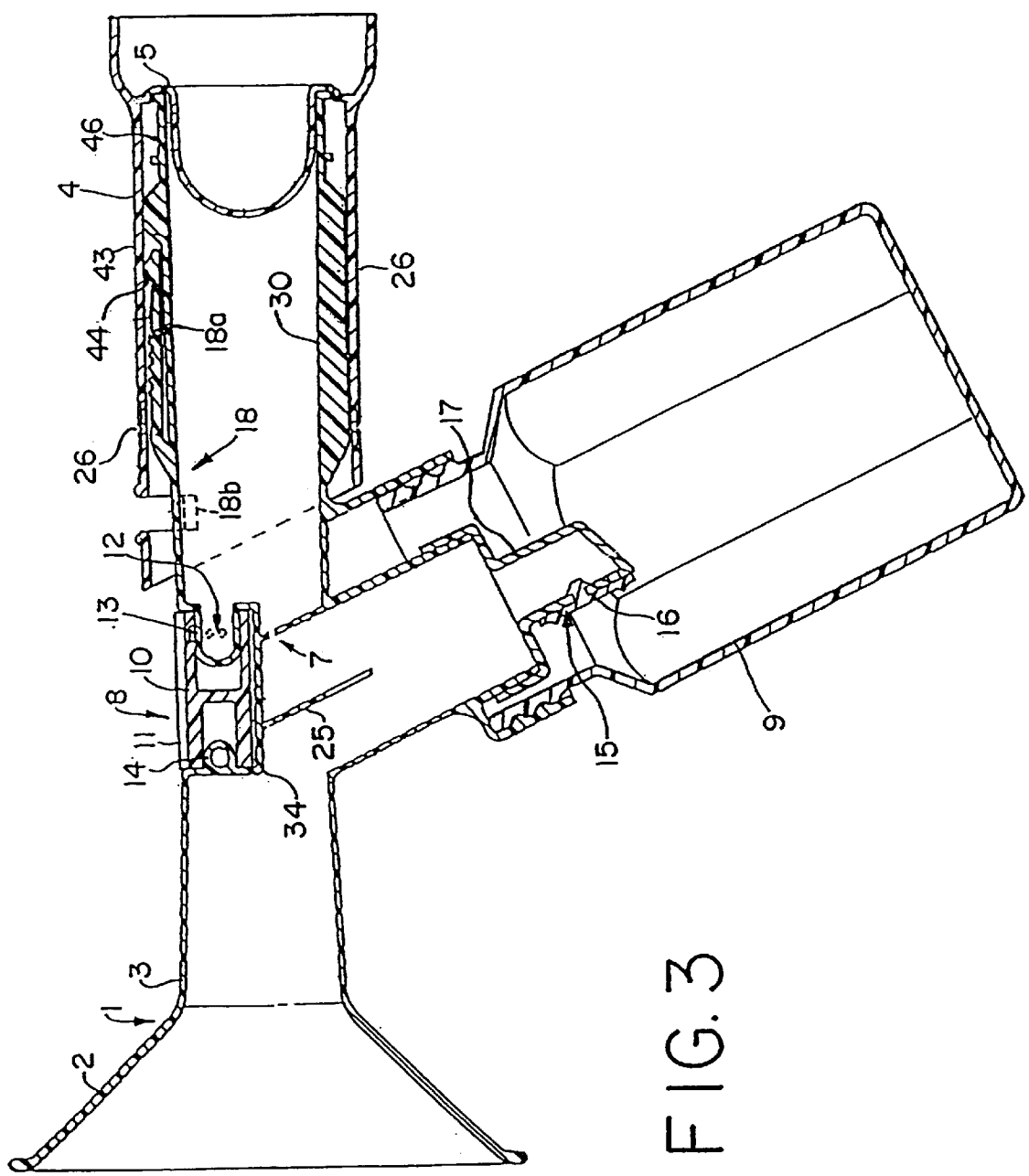
FIG. 3 is a view similar to that of FIG. 2 showing the cylinder in the position of FIG. 1.

When the cylinder 4 is reciprocated to the forward position, i.e., a compression stroke, as depicted in FIGS. 1 and 3, the increased pressure is released, such as through a mechanism as shown and described in U.S. Pat. No. 4,929,229, which is incorporated herein by reference. Vacuum is also released on the rearward stroke through vent hole 26 in the cylinder 4 which is uncovered when the pump reaches the maximum stroke, as depicted in FIG. 3. The pumping action is created by reciprocating the cylinder 4 over the pump tube 30, thereby generating intermittent vacuum that is communicated to the shield 1.

The pump tube 30 is in communication with a collection or catch chamber 6, a vacuum passage 7, and the vacuum regulator 8. The catch chamber 6 extends downwardly from the tubular extension 3, and a container 9 for holding the expressed milk is attachable thereto in a known manner.

A separation wall 25 extends downwardly from the tubular extension and in advance of the vacuum passage 7. The bottom of the separation wall 25 extends below the level of the vacuum passage 7 to block expressed milk flowing from the hood body 1 from entering the vacuum passage 7.

The vacuum regulator 8 modifies the amount of reduced pressure generated by the pumping action. The regulator 8 comprises a rotary member 10 with an internal groove or passage 32 and with plurality of raised bumps 11 (see, e.g., FIG. 4) on the surface of the rotary member having indicia thereon to indicate to the user the vacuum settings. The rotary member 10 has hollow ends. One hollow end encircles a ported structure 13 in the form of a nub that extends out of the front wall of the pump tube 30, having a pair of holes or ports 12. The rotary member 10 fits within a cavity 34 formed in the hood body 1. The ported nub 13 is at one end of the cavity, and a boss 14 is at the other end. The other hollow end of rotary member 10 is received on the boss 14 to rotate thereon. Reduced pressure is adjusted by positioning the internal groove 32 of the rotary member 10 over one, both or neither of ports 12 of the ported nub 13. The internal groove 32 is open to atmosphere. The ports 12 extend into the interior of the hood body 1. Depending upon whether the internal groove 32 is over one port or both ports 12, suction or reduced pressure is thereby modified by allowing air to bleed into the pump tube 30 through the vacuum regulator 8. The regulator 8 is easily rotated, and conveniently located, allowing the user to manipulate it with one finger, if desired.

A valve mechanism 15 is located at the lower portion of catch chamber 6. The valve mechanism 15 is described in U.S. Pat. No. 4,929,229, with a flexible disk 16 mounted to cover openings in a valve housing 17 in a flap-valve fashion. When the breast pump is operated, the disk 16 is caused to close underlying apertures in the valve housing 17 under negative pressure, thus closing the collection chamber 6. When the vacuum is released, milk collected in the collection chamber 6 flows downwardly into the container 9 through the apertures past the disk 16. The valve housing 17 may be attached to the outside of a short tubular extension of the collection chamber 6 via a snug interference fit.

A locking means 18 for preventing the cylinder from accidentally disengaging from the tubular extension is also provided. An angled latch mechanism 18a formed on the pump tube 30 is depicted in FIGS. 2 and 3. The angled latch mechanism 18a has one end integral with the pump tube 30 with a free end that can engage in a groove or slot 18b formed adjacent the open end of the cylinder 4.

FIG. 2 depicts the pump in the position when the cylinder 4 is fully reciprocated toward the rear end of the pump tube 30, i.e., the point of maximum reduced pressure, at which point the angled latch mechanism is engaged in the groove 18b. The latch 18a is resilient, and is biased to engage the inside wall of cylinder 4. The locking means 18 is designed to allow the user to selectively disengage the cylinder 4 from the pump tube 30. A surface 43 of the latch mechanism 18a is angled in ramp-like fashion so that cylinder 4 can slide over the angled latch mechanism 18a when the cylinder 4 is moved over the pump tube 30 to the forward position (compression). The angled latch mechanism 18a also has a vertical edge 44 extending upward at the end of the angled latch mechanism 18a which vertical edge catches in the groove 18b of the locking means 18 to prevent the cylinder 4 from disengaging from the pump tube 30 as the cylinder 4 completes the maximum stroke. Latch 18 can be depressed in the locked position to allow the cylinder to be removed from the pump tube 30.

Figure 5:
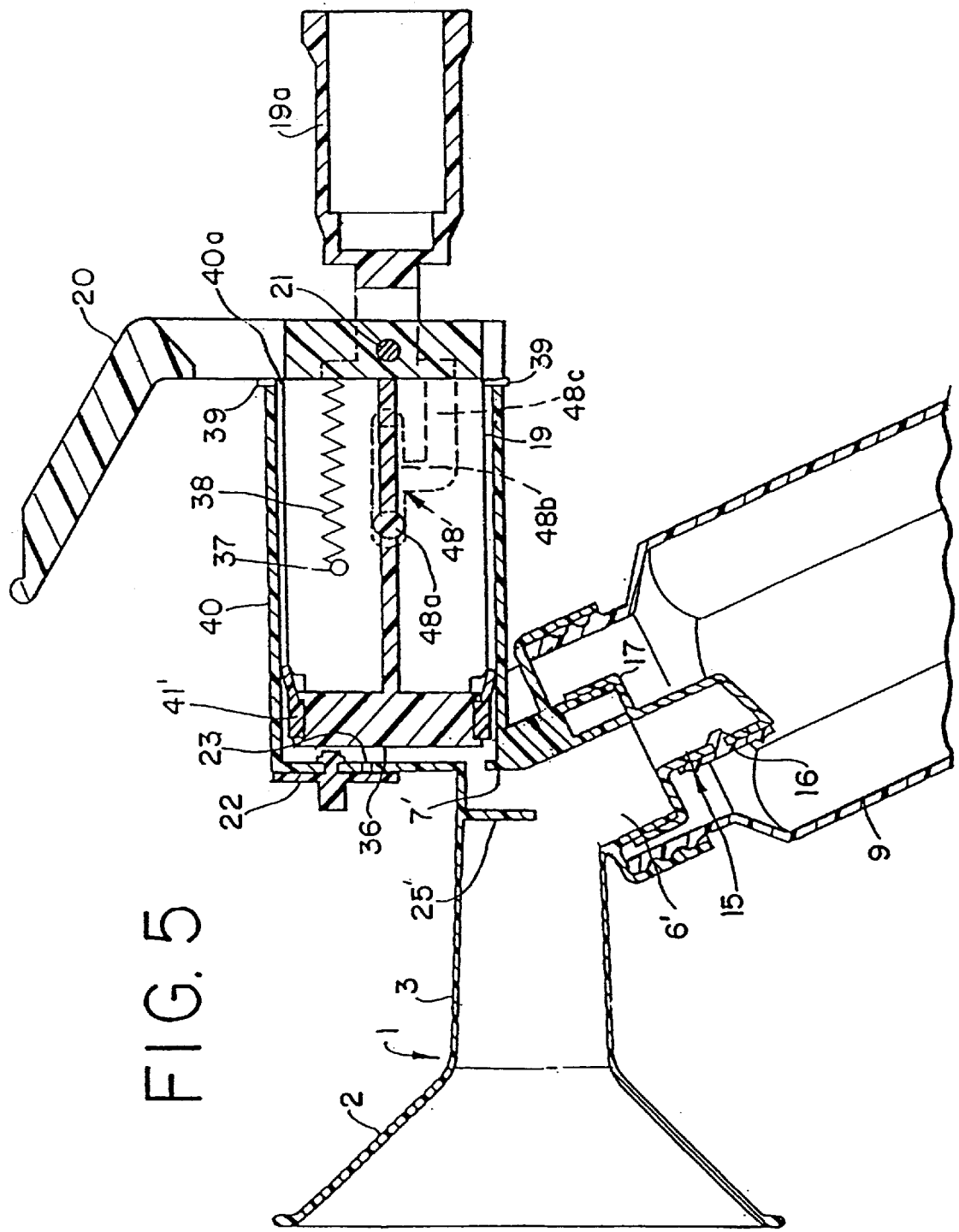
FIG. 5 is a side elevational sectional view of a second embodiment made in accordance with the present invention showing the piston rod in the relaxed or start position.
Figure 6:
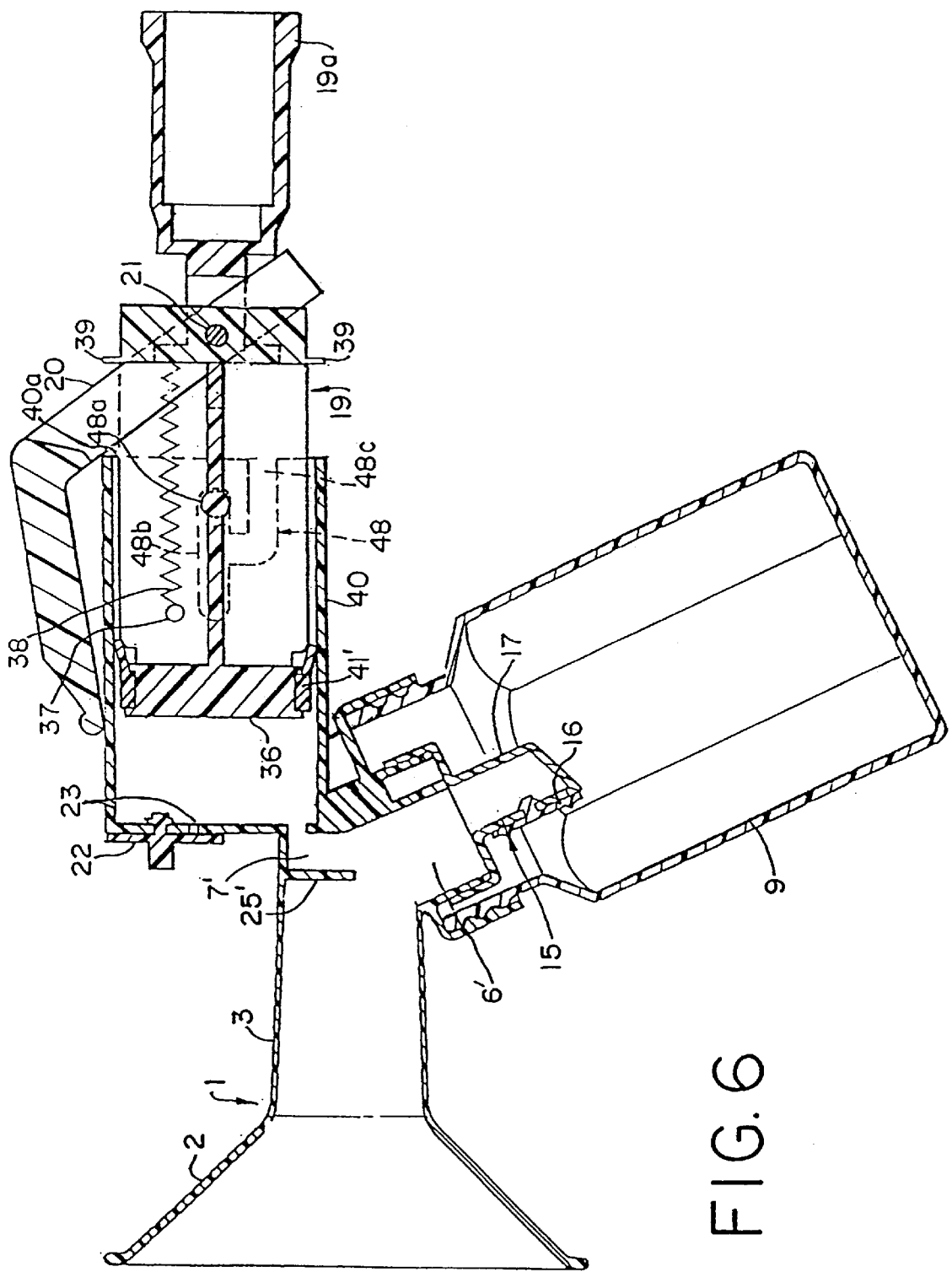
FIG. 6 is a vertical sectional view of the second embodiment showing the position of the lever and the piston rod of the one-hand-operated breast pump when the piston rod is in the position where the maximum amount of reduced pressure is created.

In another embodiment, depicted in FIGS. 5 and 6, the breast pump is designed for one-handed or two-handed operation. It will be noted that in this as well as all embodiments herein, like numbers are used for substantially identical parts. Prime and double prime numbers are used for similar but modified parts.

In this second embodiment, a piston rod 19 has a piston 36 which is reciprocated within a pump cylinder 40. A tubular extension 3 of the hood body 1 in this second embodiment is in communication with a collection chamber 6', a vacuum passage 7', and the cylinder 40. The piston rod 19 is received within the cylinder 40 and creates a vacuum as the piston rod 19 reciprocates the piston 36 within the cylinder 40. A gasket 41' is provided in an annular groove formed around the piston 36 to sealingly engage the interior sidewall of the cylinder 40.

A lever 20 is pivotally mounted on the piston rod 19 via a pin 21. The lever 20 allows the user to operate the pump efficiently and easily using one hand to move the lever 20 to reciprocate the piston rod 19 within the cylinder 40. When the user squeezes the lever 20 from the position of FIG. 5 to a position adjacent or against the cylinder 40, the lever 20 uses the end edge 40a of the cylinder 40 as a fulcrum to move the piston rod 19 outwardly from the cylinder 40, as depicted in FIG. 6, thereby creating reduced pressure within the pump. The lever 20 could be returned to the position in FIG. 5 through manipulation of a handle 19a to push the piston rod 19 back into the cylinder 40, but preferably a spring return can be used to pull the piston rod 19 back to its forward position, fully received within the cylinder 40. The spring return may be located within the cylinder 40 and may comprise a spring 38, one end of which is mounted on a post 37 inside the cylinder 40. The other end of the spring 38 is mounted on a flange 39 extending from the piston rod 19 adjacent the pin 21.

By positioning of the lever 20 in relation to the cylinder 40 so that the pumping action is created by the user closing her hand around the lever 20 and cylinder 40, the pump is ergonomically designed to rely on more correct muscle groups in the user's hand to create and maintain the pumping action. Utilizing the correct muscle groups is important so that the user does not tire or cramp during the pumping process. Fatigue leads to fluctuations in the pumping pressure, which causes ineffective and inefficient pumping.

In this embodiment, an air release flap valve 22 (similar to that in U.S. Pat. No. 4,929,229) covers one or more apertures 23 at the front of cylinder 40 to allow air to escape from the cylinder 40 on the forward (compression) stroke.

A locking means 48 is incorporated into the pump to prevent the piston rod 19 from accidentally disengaging from the cylinder 40 as it is moved toward the open end 40a of the cylinder 40. The locking means comprises a channel 48b on the cylinder 40 in which a pin 48a extending outwardly from the piston travels. The channel 48b allows the piston rod 19 to reciprocate in the manner described. To selectively disengage the piston rod 19 from the cylinder 40, the pin 48a exits through a J-shaped section of channel 48c by aligning the pin with a portion of the J-shaped channel communicating with channel 48b and rotating and then removing the piston rod 19 causing the pin to move through the channel portion 48c.

As in the first embodiment, the collection chamber 6' extends downwardly from the tubular extension 3, and a container 9 for holding the expressed milk is attachable thereto. A separation wall 25' extends downwardly from the tubular extension and in advance of the vacuum passage 7'. The bottom of the separation wall 25' extends below the level of the vacuum passage 7' to block expressed milk flowing from the hood body 1 from entering the vacuum passage 7. Similarly, a valve mechanism 15, preferably of the type and for the purpose described in the first embodiment, is located at the lower portion of collection chamber 6.

This embodiment may also be adapted to utilize a vacuum regulator. For example, a regulator of the type shown in U.S. Pat. No. 4,857,051 may be readily adapted for use with this pump.

One-handed operation of the breast pump of FIGS. 5 and 6 has thus been described. The breast pump is also adapted for two-handed operation, should the user so desire. This is accomplished through the provision of a graspable extension 19a on the piston rod 19. The extension or grip 19a is made for the user to be able to grasp the same and push and pull it to reciprocate the piston 36. Obviously, with a spring-return mechanism such as shown with the lever mechanism 20, the user would simply need to pull the grip formed by the extension 19a, and then allow it to return under influence of the spring 38. Two modes of manually operating the pump are thereby provided.

In a third embodiment of a manually operable breast pump, as shown in FIGS. 7–15, the breast pump has a hood body 1 having two sections: a funnel shaped front section 2 and a tubular extension 3 extending therefrom. Like the first embodiment, a pump tube 30' is in communication with the tubular extension 3 of the hood body 1. A cylinder 4' with end cap 5' is slidably engaged over the pump tube 30'. The end cap 5' herein has an end portion 50 which extends into the cylinder 4' reducing the air space in the cylinder 4' to a desired volume. The end cap 5' can be made removable from the cylinder 4; for cleaning.

When the cylinder 4' is reciprocated to the rear end of the pump tube 30' with an annular groove 46, reduced pressure or vacuum is created. When the cylinder 4' reaches the position of maximum stroke, a vent hole (or holes) 26 is uncovered, releasing the vacuum. The pumping action is created by reciprocating the cylinder 4' over the pump tube 30', thereby generating intermittent vacuum. A flexible gasket ring 41 fits over the rear end of the pump tube 30' in groove 46 to seal the pump tube to the cylinder 4' in a sliding engagement.

The pump tube 30' is in further communication with a collection chamber 6", a vacuum passage 7", and a vacuum regulator 8. The collection chamber 6" extends downwardly from the tubular extension 3, and a container 9 for holding the expressed milk is attachable thereto in a known manner.

A separation wall 25" extends downwardly from the tubular extension and in advance of the vacuum passage 7". The bottom of the separation wall 25" extends below the level of the vacuum passage 7" to block expressed milk flowing from the hood body 1 from entering the vacuum passage 7".

The vacuum regulator 8 (FIG. 7) is positioned on the outer wall of the hood body 1, and specifically in this embodiment, on the outer wall of the tubular extension 3, and functions in the same manner as described in detail in the first embodiment of this invention. Similarly, a valve mechanism 15, preferably of the type and for the purpose described in the first embodiment, is located at the lower portion of collection chamber 6.

In this embodiment, another locking means is used. A post or tooth 27 (FIGS. 9–11) extends downwardly from the top of the inner wall of the cylinder 4' adjacent the front end of the cylinder 4'. As the cylinder is engaged over the pump tube 30', the post 27 is directed into a portion of a J-shaped channel 58c formed on the exterior of pump tube 30'. The post 27 travels along channel 58c, and is then rotated (via the cylinder 4') so that the post 27 can travel into a second channel 58b on the outside of the cylinder. During the pumping action, the post 27 reciprocates within the second channel 58b, which prevents the cylinder 4' from accidentally disengaging from the pump tube 30'. The cylinder 4' can be selectively removed for cleaning by directing the post 27 back out through channel 58c.

A shield insert 42 may be inserted into the funnel-shaped section of the hood body or breast shield 1 of this embodiment, or any of the preceding embodiments. For example, this insert 42 may be of the type used to adapt the breast shield for smaller breasts.

The flexible gasket ring 41 can be placed on the annular groove 46 of the pump tube 30' during extended periods of storage without risk that it may become deformed or take a set, because the diameter of the cylinder 4' is increased slightly in the area at point 45 on the cylinder where the cylinder, when fully engaged over the length of the pump tube 30', would be positioned over the gasket 41 and pump tube 30' during storage.

While the invention has been described with reference to particular embodiments, those having skill in the art will recognize modifications of elements and structure which may facilitate the application of the invention, but which still fall within the scope of the invention. For instance, while this invention has been described in an environment of a breast pump, it could be utilized in other applications.

I claim:

1. A vacuum regulator for a breast pump, comprising:
   a nub having at least one port, said nub adapted to be in communication with a volume of said breast pump within which a negative pressure is periodically generated; and
   a rotary member having an internal groove, said rotary member being rotatably received over said nub, whereby said internal groove of said rotary member is open to atmosphere and is selectively positionable over said at least one port of said nub to adjust vacuum pressure by allowing air to pass to said volume when over said port and not to pass when not over said port.

2. The vacuum regulator of claim 1, wherein said rotary member can be manipulated by a single finger of the user.

3. The vacuum regulator of claim 2, wherein said vacuum regulator further comprises a plurality of raised formations on the outer surface of said rotary member, at least one but not all of said raised formations being positioned over said internal groove, said formations indicating the varying positions of the internal groove over said ports.

4. The vacuum regulator of claim 3, wherein said vacuum regulator is located on a hood body of a breast pump.

5. The vacuum regulator of claim 4, wherein said one or more ports of said nub are in communication with the interior of said hood body.

6. In a breast pump having a hood body that includes a funnel-shaped portion within which a breast is received and a tubular extension, the improvement comprising:
   a vacuum regulator located in a cavity in the hood body, said regulator having a plurality of positions at which different respective vacuum levels can be set by an operator, said regulator capable of maintaining a set vacuum level when released by said operator, said regulator including an open channel through which atmospheric air can flow but is regulated by operation of said regulator to the respective vacuum levels.

7. The breast pump of claim 6, said vacuum regulator further comprising:
   a ported structure having one or more ports, said one or more ports being in communication with the interior of said hood body;
   a rotary member rotatably received on said ported structure, said rotary member having an internal groove selectively positionable over said one or more ports, said internal groove being in communication with the atmosphere; and
   a plurality of raised formations on the surface of said rotary member, said formations indicating the varying positions of the internal groove over said ports.

8. The breast pump of claim 7, wherein said ported structure is a nub and said rotary member is capable of being rotated with a single finger of the breast pump user during operation of said breast pump.

* * * * *